United States Patent [19]
Savage et al.

[11] Patent Number: 5,281,212
[45] Date of Patent: Jan. 25, 1994

[54] LASER CATHETER WITH MONITOR AND DISSOLVABLE TIP

[75] Inventors: Steven D. Savage, Brooklyn Center; Gregory G. Brucker, Minneapolis, both of Minn.

[73] Assignee: Angeion Corporation, Minneapolis, Minn.

[21] Appl. No.: 836,227

[22] Filed: Feb. 18, 1992

[51] Int. Cl.$^5$ ............................................... A61B 5/04
[52] U.S. Cl. .................................... 606/15; 606/14; 604/265
[58] Field of Search ............... 606/2, 3, 7, 11, 14, 606/15, 16, 31, 48, 76, 108, 129; 604/20, 21, 265; 128/4, 5, 6, 7, 8, 395, 396, 397, 398, 736

[56] References Cited

U.S. PATENT DOCUMENTS

| | | | |
|---|---|---|---|
| 3,736,939 | 6/1973 | Taylor | 604/265 |
| 4,669,467 | 6/1987 | Willett et al. | 128/303.1 |
| 4,718,417 | 1/1988 | Kittrell et al. | 128/303.1 |
| 4,785,806 | 11/1988 | Deckelbaum | 128/303.1 |
| 4,785,815 | 11/1988 | Cohen | 606/15 |
| 4,860,743 | 8/1989 | Abela | 606/7 |
| 4,985,028 | 1/1992 | Isner et al. | 606/15 |
| 4,997,431 | 3/1992 | Isner et al. | 606/15 |

Primary Examiner—Stephen C. Pellegrino
Assistant Examiner—Mike Peffley
Attorney, Agent, or Firm—Patterson & Keough

[57] ABSTRACT

A laser catheter for irradiation of human myocardial tissue containing a fixed feedback mechanism for monitoring the damage created by laser irradiation, and which is usable with standard catheters designed for angiography and angioplasty. Means for sensing distal temperature are provided in the form of a plurality of thermocouples, along with the ability to cool the fiber optic and distal tip with a flushing solution. Flushing of the area adjacent to the tip is provided for by a fluid which travels the length of the laser catheter. A dissolvable tip covering at the distal end facilitates passage of a very sharp point through a guiding catheter or vasculature.

29 Claims, 3 Drawing Sheets

LASER CATHETER WITH MONITOR AND DISSOLVABLE TIP

CROSS REFERENCE TO CO-PENDING APPLICATIONS

U.S. patent application Ser. No. 07/608,281, filed Nov. 2, 1990, and U.S. patent application Ser. No. 07/608,290, filed Nov. 2, 1990, are commonly assigned to the assignee of the present invention.

BACKGROUND OF THE INVENTION

1. Field of the Invention

The present invention pertains to a medical device for use in therapy of a patient, and more particularly, pertains to a catheter for use in association with laser irradiation.

2. Description of the Prior Art

It is known in the art to use laser energy for medical purposes. A common medical application is in the irradiation of myocardial tissue. For external use, the laser energy may be directly applied. However, when the procedure requires irradiation of tissue which is not readily accessible, the use of a laser catheter is common. A typical application for a laser catheter is in the cardiovascular system. U.S. Pat. Nos. 4,997,431 and 4,985,028, both issued to Isner et al., show laser catheters particularly adapted for laser irradiation of tissue within the cardiovascular system.

The irradiation of tissue must be accomplished with great precision as the danger of also damaging necessary adjacent tissue is always present, especially when the process occurs remotely at the distal end of a relatively long catheter. U.S. Pat. No. 4,785,806 issued to Deckelbaum discusses a system whereby an attempt is made to distinguish different types of tissue using ultra violet fluoroscopy. A similar approach is proposed in U.S. Pat. No. 4,718,417 issued to Kittrell et al. Spectral analysis of reflected light energy is also proposed in U.S. Pat. No. 4,669,467 issued to Willett et al.

However, none of these approaches directly monitor the absorption of the energy by the tissue. It is the production and absorption of laser radiation which produces controlled heating and actually damages the unwanted tissue. The prior art discusses distinguishing the tissue prior to laser irradiation and analyzing the products of the procedure following irradiation, but none of the references measure the absorption activity directly during the laser irradiation process.

SUMMARY OF THE INVENTION

The present invention overcomes the disadvantages found in the prior art systems by providing a medical irradiation catheter having means for directly monitoring the heat produced during the procedure. The sensors may be optionally coupled to external electronic circuitry to produce a safety alert or directly alter the energy to be applied.

According to one embodiment of the present invention, there is provided a catheter where a central lumen consists of a plastic tube approximately 100 cm long to which is affixed, at its distal end, a metallic or plastic tip. The tip consists of two components: one is a central lumen for placement and fixation of a single optical fiber, and the second is a small hypodermic, stainless steel tube to which is attached multiple temperature sensors such as thermocouples. The temperature sensors are affixed to the inside of the hypodermic tubing at predetermined locations from the tip of the catheter. The hypodermic tubing is welded to the tip to firmly establish the hypodermic tubing to the tip and fix the relationship between the temperature sensors and a laser fiber. The temperature sensors are designed such that they are electrically isolated from the hypodermic tubing, which serves as one pole of a bipolar sensing electrode system. The other pole is the tip of the catheter.

To be effective, the sharp hypodermic tubing must protrude as the distal most portion of the catheter system. However, great difficulty in advancing the catheter to the target site would be anticipated in view of the circuitous pathway of the vascular system. To mitigate the problems associated with catheter placement, a system according to the present invention may be supplied with a dissolvable covering over the distal tip of the catheter. This covering protects the vessel walls during advancement of the catheter by providing the distal end with a smoothly rounded tip. In a short while, the tip material is dissolved exposing the sharp hypodermic tubing for insertion into the tissue at the target site.

It is preferable to provide a catheter having means for providing a cooling fluid, such as sterile saline solution, to the area under treatment. This tends to protect adjacent tissue through the absorption and dissipation of excess heat. Temperature sensors are particularly important in controlling the amount of flow and directionality of such coolants.

It is also desirable to provide a flushing lumen within the ablation catheter. This feature permits removal of debris, which may have been generated or released by the ablation process. Again, it is most useful to monitor temperature of the target site as the flushing activity is in process.

Significant aspects and feature of the present invention include a medical laser catheter system having means for directly monitoring operation during a procedure. This provides the attending medical personnel with useful data in the conduction of the procedure and may serve as an important safety feature. During catheter placement, the vascular system is protected from damage by the sharp monitoring apparatus by a smooth covering which promptly dissolves at the target site.

Having thus described the embodiments of the present invention, it is the principal object hereof to provide a medical laser catheter with temperature sensing means, cooling means, a dissolvable smooth tip, and flushing means.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
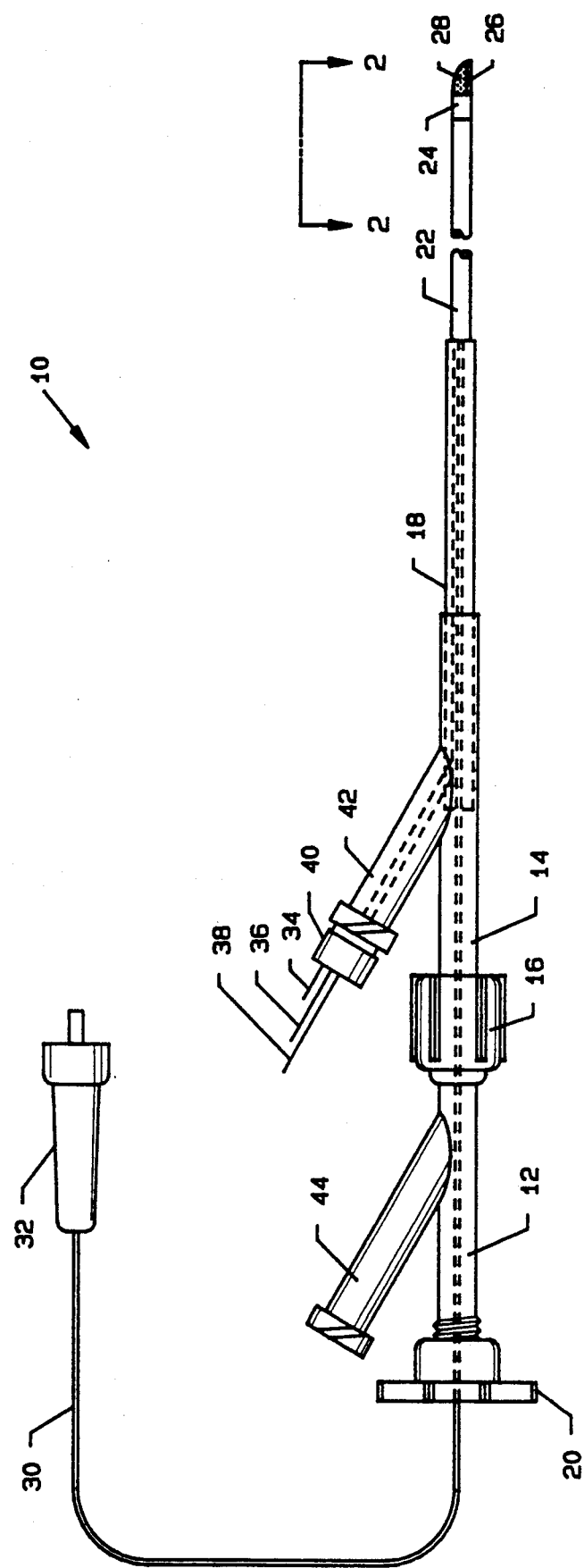
FIG. 1 illustrates a plan view of a medical ablation laser catheter, the present invention.

FIG. 1 illustrates a plan view of a medical laser catheter 10. The laser catheter 10 includes Y-connectors 12 and 14 coupled to each other by a coupler nut 16. A stainless steel tube 18 is affixed to and extends from one end of the Y-connector 14. A Touhy-Borst connector 20 is positioned at the proximal end of the Y-connector 12. Plastic catheter tube 22 is about 100 cm long, and is secured into one end of the stainless steel tube 18. Annular metallic tip 24 is secured to the distal end of the plastic catheter tube 22. A stainless steel hypodermic tube 26 extends from the metallic tip 24, and an organic dissolvable material 28 is placed over the hypodermic tube 26 adjacent to the metallic tip 24. A fiber optic cable 30 passes through the Touhy-Borst connector 20, the Y-connectors 12 and 14, the stainless steel tube 18, and the plastic catheter tube 22 and connects to the metallic tip 24. A standard optical connector 32 attaches to the proximal end of the fiber optic cable 30. A plurality of wires including wires 34, 36 and 38 pass through a seal 40 and the port 42 of the Y-connector 14. They pass through the stainless steel tube 18 and plastic catheter tube 22 and are connected to the annular metallic tip 24 and hypodermic tube 26 as later described in detail. A flushing port 44 extending from the Y-connector 12 is connected t the interior regions of the Y-connectors 12 and 14, and more importantly, to the interior lumens of the stainless steel tube 18 and the plastic catheter tube 22. A flushing fluid is routed through the Y-connectors 12 and 14 and along the fiber optic cable 30, through the tubes 18 and 22 and out of the annular metallic tip 24.

Figure 2:
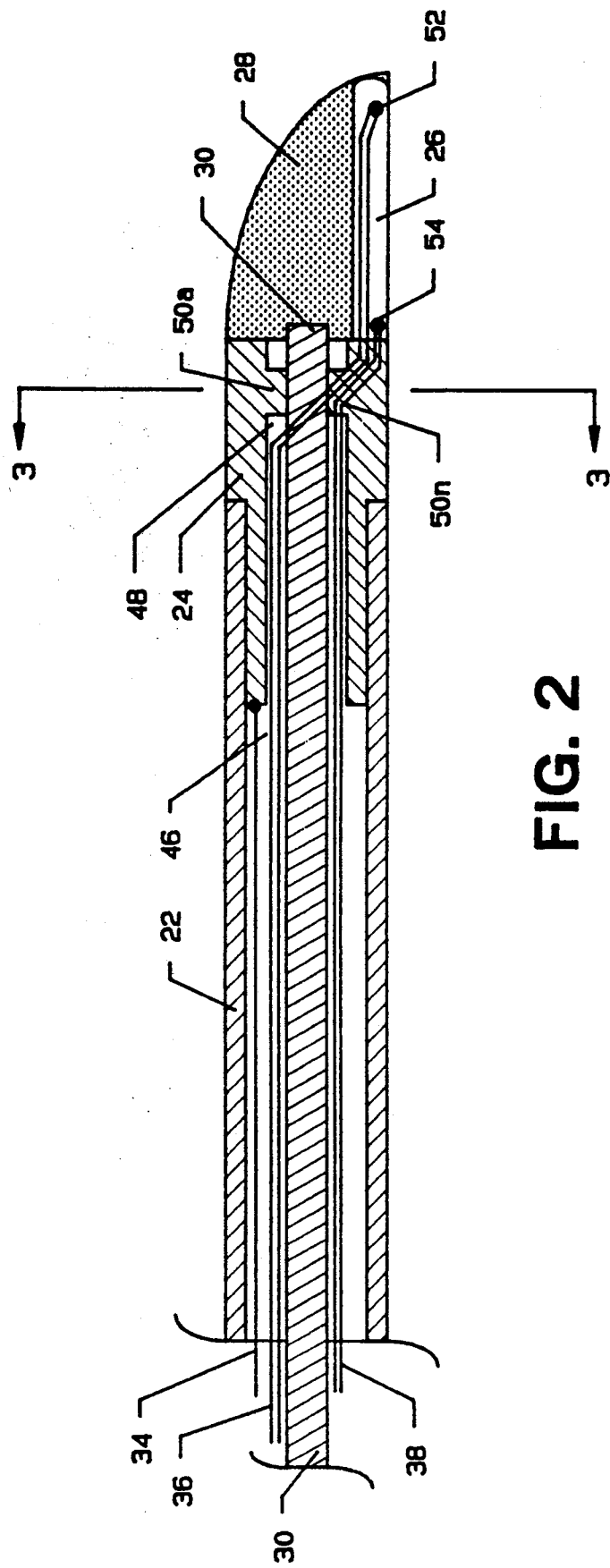
FIG. 2 illustrates a cross-sectional view of the catheter tip area along line 2—2 of FIG. 1; and, FIG. 3 illustrates a cross-sectional view along line 3—3 of FIG. 2.
Figure 3:
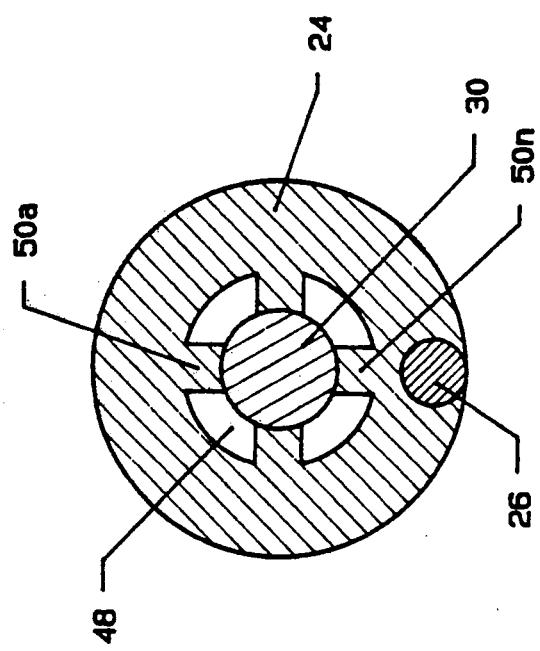

FIG. 3 illustrates a Cross-sectional view along line 3—3 of FIG. 2 where all numerals correspond to those elements previously described. Illustrated in particular are the support struts 50a-50n which center the fiber optic cable 30 in the lumen 48. The sterile saline solution passes through the lumen 48 and around the struts 50a-50n to purge blood from the field of view of the fiber optic cable 30 and to cool the tissue adjacent the ablation area.

FIG. 2 illustrates a cross-sectional view of the catheter tip area along line 2—2 of FIG. i where all numerals correspond to those elements previously described. The metallic tip 24 is multi-radiused so that the lesser radius will frictionally engage the lumen 46 of the plastic catheter tube 22. The metallic tip 24 includes a lumen 48, which has a plurality of support struts 50a-50n about the lumen 48 for support of the distal end of the fiber optic cable 30. During the procedure, energy is radiated from the distal end of fiber optic cable 30.

Wire 34 is connected to the metallic tip 24 and passes through the lumen 46 to the Y-connector 14 as previously described. This permits electrical sensing of the biological tissue in contact with the metallic tip 24. The hypodermic tube 26 secures in the bottom portion of the annular metallic tip 24, but is insulated from it. Hypodermic tube 26 includes thermocouples 52 and 54 embedded or otherwise attached thereto. The wires 36 and 38 connect electrically to the thermocouples 52 and 54, respectively, and are routed through the interior of the hypodermic tube 26, lumen 48, and lumen 46 to the Y-connector 14 as previously described. This permits direct temperature measurement of the laser irradiated area at more than one tissue depth. The hypodermic tube 26 contains a plurality of thermocouples including the thermocouples 52 and 54, which also provide for an electrical connection to permit electrical sensing of the biological tissue in the area of tissue irradiation. The metallic tip 24 provides the second pole of the electrophysical monitoring system when used in a bipolar configuration. Specifically, bipolar mapping can be carried out by measuring local activation potentials of the endocardial surface. In conjunction with standard EP monitoring equipment, the signals generated can be used to determine electrophysiological properties of the tissue that lies between the electrodes. During laser ablation, the signals can be watched for changes.

The annular space between the plastic catheter tube 22 and the fiber optic cable 30 serves as a conduit for a flushing medium such as sterile saline solution. This liquid cools the tissue and the metallic tip 24, and also removes blood from the field of laser energy during the irradiation process. As explained above, this tends to protect tissue directly adjacent to the irradiated area.

Because of the fixed relationship between hypodermic tube 26 and the metallic tip 24, and because of the need for catheter 10 to pass through the tortuous passageway of the cardiovascular system, the metallic tip 24 and hypodermic tube 26 ar coated with a biologically compatible organic dissolvable material 28, such as a glycerine based solid, or a glucose solution that is cast onto tip 24 so as to cover hypodermic tube 26 and cable 30, and is dried. Preferably, the dissolvable material dissolves in the biological medium (such as blood) in about ten minutes or less. The operative factor is allowance of sufficient time before tube 26 and/or cable 30 is exposed to feed the catheter through the vascular system to the desired location. Organic dissolvable material 28 dissolves in the presence of blood. Such a coating allows the very sharp point of hypodermic tube 26 to be placed on the end of the metallic tip 24 and yet easily pass through a guiding catheter or the vascular system. However, in the presence of blood, the biologically compatible organic dissolvable material 28 dissolves and allows the hypodermic tube 26 to penetrate the tissue to monitor temperature at various tissue depths. Hypodermic tube 26 also acts as a fixation wire after penetrating the tissue surface.

MODE OF OPERATION

Catheter 10 is inserted percutaneously into the vascular system through a puncture or standard introducer. The distal end is advanced under fluoroscopy to the site of the tissue to be irradiated. After the biologically compatible dissolvable organic material 28 has been dissolved by contact with the blood, the hypodermic tube 26 is advanced into the tissue until the distal end of fiber optic cable 30 and metallic tip 24 are in contact with the intended tissue. Laser energy is applied to the proximal end of fiber optic cable 30 through standard optical connector 32.

The temperature is monitored at the various tissue depths by thermocouples 52 and 54. The supply of laser energy is interrupted if the temperature at any level exceeds a given safety threshold. The electrical activity of the irradiated area is monitored using the bipolar sensing system consisting of hypodermic tube 26 as a first electrode and metallic tip 24 as the second electrode.

Having thus described the preferred embodiments of the present invention, those of skill in the art will readily appreciate the many additional embodiments which can be made and used in accordance with the teachings found herein and within the scope of the claims hereto attached.

We claim:

1. A body tissue irradiation catheter comprising:
   a. a catheter body having a distal end and a proximal end;
   b. an optical fiber in said catheter body for delivering laser energy to said tissue;
   c. a tip having a proximal end and a distal end, said tip proximal end being coupled to said distal end of said catheter body, said tip comprising a central lumen of a diameter larger than the diameter of said optical fiber;
   d. penetrating means coupled to the distal end of said tip for penetrating the tissue to stabilize the catheter; and
   e. temperature sensing means for sensing the temperature of said body tissue during irradiation, said temperature sensing means being positioned on said penetrating means so that the sensed temperature is used to control the amount and duration of laser energy applied to the tissue.

2. The catheter of claim 1 wherein said temperature sensing means comprises a plurality of thermocouples positioned at different points inside said penetrating means for sensing the temperature at different depths in said tissue.

3. The catheter of claim 10 wherein said penetrating means has a distal end and a proximal end, said distal end of said penetrating means comprising a surface sufficiently sharp so as to penetrate said tissue.

4. The catheter of claim 1, wherein said tip is metallic.

5. The catheter of claim 1, wherein said temperature sensing means is positioned on said penetrating means so that the temperature of the tissue may be measured at different penetration depths.

6. The catheter of claim 5, wherein said penetrating means is an electrode.

7. The catheter of claim 6, wherein said penetrating means is used as an electrophysiological sensing means for monitoring tissue electrical potential characteristics in a unipolar mode.

8. The catheter of claim 7, in which the tip and the penetrating means comprise electrodes for sensing tissue electrical potential characteristics in a bipolar mode.

9. The catheter of claim 1, further comprising flushing means within said catheter for removal of biological debris.

10. The catheter of claim 1, wherein said optical fiber is supported in said central lumen by a plurality of struts extending into said central lumen and engaging said optical fiber.

11. The catheter of claim 1, further comprising a biologically compatible, dissolvable material covering said penetrating means.

12. Apparatus for irradiating internal bodily tissue, comprising:
   a. a catheter body having a proximal end and a distal end;
   b. an optical fiber in said catheter body, said optical fiber having a proximal end and a distal end;
   c. laser energy generation means in communication with said proximal end of said optical fiber for generating laser energy;
   d. a tip secured to said distal end of said catheter body, said tip housing said distal end of said optical fiber, said tip including a hypodermic tube extending axially therefrom; and,
   e. a coating on said tip so as to cover said hypodermic tube and said distal end of said optical fiber, said coating being dissolvable in bodily fluid.

13. The apparatus of claim 12, wherein said tip comprises a lumen having a plurality of support struts thereabout for supporting said distal end of said optical fiber housed therein.

14. The apparatus of claim 12, further comprising electrophysiological sensing means in communication with said tip.

15. The apparatus of claim 14, wherein said hypodermic tube is insulated from said tip.

16. The apparatus of claim 12, wherein said hypodermic tube includes temperature sensing means for sensing the temperature of said bodily tissue.

17. The apparatus of claim 16, wherein said temperature sensing means comprises a plurality of thermocouples attached to said hypodermic tube at different points along the axial length thereof.

18. The apparatus of claim 17, further comprising flushing means for removal of biological products from the field of view of the laser energy generation means.

19. The method of directing a catheter percutaneously into the vascular system of a warm-blooded animal, comprising:
   a. providing a catheter body having a proximal end, a distal end and a lumen therein, said catheter body housing a fiber optic cable in said lumen, said cable having a proximal end and a distal end, said proximal end being in communication with laser energy generation means, and a metallic tip secured to said distal end of said catheter body, said metallic tip housing said distal end of said cable, said metallic tip including a hypodermic tube extending axially therefrom;
   b. forming a coating on said metallic tip so as to cover said hypodermic tube and said distal end of said cable, said coating being dissolvable in the bodily fluid of said warm-blooded animal;
   c. routing said catheter body under fluoroscopy through said vascular system to a desired location in said warm-blooded animal prior to sufficient dissolution of said coating which would expose said hypodermic tube and said cable distal end; and,
   d. allowing for the complete dissolution of said coating.

20. The method of claim 19, further comprising ablating tissue at said desired location upon said dissolution of said coating.

21. The method of claim 20, further comprising monitoring the electrophysiological activity of said tissue.

22. The method of claim 20, further comprising monitoring the temperature of said tissue at various tissue depths during said ablation.

23. The method of claim 22, further comprising interrupting said ablation if said monitored temperature exceeds a predetermined safety threshold.

24. A method of directing and controlling a laser irradiation catheter percutaneously in the vascular system, comprising:
   providing a catheter with a tip having a proximal and a distal end, the distal end comprising temperature sensing means for sensing the temperature of tissue within said vascular system during laser irradiation;
   b. coating the distal end with a material dissolvable in the medium within which it is inserted;

c. routing said catheter distal end through said vascular system to a desired location prior to dissolution of said coating;
d. allowing for the complete dissolution of said coating; and,
e. sensing the temperature of the tissue and controlling the amount and duration of laser energy applied to the tissue depending on the sensed temperature.

25. The method of claim 24 wherein said coating encapsulates said distal end whereby said distal end is devoid of protuberances, thereby facilitating entry of the catheter into the vascular system.

26. A method of irradiating internal body tissue with a laser catheter comprising:
   a. directing the catheter to the region of the body tissue;
   b. puncturing the tissue to a desired depth;
   c. inserting a first temperature monitor to a first depth within said puncture;
   d. irradiating said tissue with said laser;
   e. during irradiation, monitoring the temperature of said first depth; and,
   f. controlling the irradiation as a function of temperature.

27. The method of claim 26 further comprising contacting said tissue with two electrodes and monitoring the electrophysiological properties of tissue during irradiation.

28. The method of claim 26 further comprising inserting a second temperature monitor to a second depth within said puncture and monitoring temperature at said second depth during irradiation.

29. The method of claim 28, further comprising flushing means for removing biological products.

* * * * *

UNITED STATES PATENT AND TRADEMARK OFFICE
CERTIFICATE OF CORRECTION

PATENT NO. : 5,281,212
DATED : Jan 25, 1994
INVENTOR(S) : Steven D. Savage

It is certified that error appears in the above-indentified patent and that said Letters Patent is hereby corrected as shown below:

Column 3, Line 44 should read: FIG. 1

Column 3, Line 28 should read: connected to the interior regions

Column 3, Line 34 paragraph beginning FIG. 3 should be moved after FIG. 2

Column 6, Line 62, should read: tip having a proximal end

Signed and Sealed this

Eighteenth Day of October, 1994

Attest:

BRUCE LEHMAN

Attesting Officer    Commissioner of Patents and Trademarks